United States Patent [19]

Chang et al.

[11] Patent Number: 5,334,708

[45] Date of Patent: Aug. 2, 1994

[54] METHOD FOR RADIOLABELING MONOVALENT ANTIBODY FRAGMENTS

[75] Inventors: Chien-Hsing Chang, Downingtown, Pa.; Anastasia L. Jones, Clinton, N.J.

[73] Assignee: Immunomedics, Inc., Warren, N.J.

[21] Appl. No.: 987,563

[22] Filed: Dec. 8, 1992

Related U.S. Application Data

[63] Continuation of Ser. No. 518,707, May 7, 1990.

[51] Int. Cl.$^5$ ............................................. C07K 15/28
[52] U.S. Cl. .................................. 530/391.5; 436/547; 436/548; 530/387.1; 530/388.1; 530/391.3; 530/404
[58] Field of Search .................... 424/1.1, 85.8; 530/391.3, 402, 391.5, 387.1, 388.1, 402, 404; 436/547, 548

[56] References Cited

U.S. PATENT DOCUMENTS

| | | | |
|---|---|---|---|
| 4,059,571 | 11/1977 | Tomibe et al. | 530/389.5 |
| 4,638,049 | 1/1987 | Masuho et al. | 530/391.9 |
| 5,011,676 | 4/1991 | Thakur | 530/388.7 |
| 5,061,641 | 10/1991 | Schochat et al. | 530/403 |

FOREIGN PATENT DOCUMENTS 0237150 9/1987 European Pat. Off.

*Primary Examiner*—George C. Elliott
*Attorney, Agent, or Firm*—Foley & Lardner

[57] ABSTRACT

A method for radiolabeling a monovalent Fab or Fab' antibody fragment which comprises the steps of cleaving a divalent F(ab)$_2$ or F(ab')$_2$ antibody fragment using sulfite or meta-bisulfite ions to produce a monovalent fragment having a free sulfhydryl group, and contacting the monovalent fragment with a cation of a metallic radionuclide which binds to sulfhydryl groups, without removing excess sulfite or metabisulfite.

22 Claims, No Drawings

METHOD FOR RADIOLABELING MONOVALENT ANTIBODY FRAGMENTS

This application is a continuation of application Ser. No. 07/518,707, filed May 7, 1990.

BACKGROUND OF THE INVENTION

The present invention relates to an improved method and kit for direct radiolabeling of a monovalent antibody fragment with a radiometal ion of a radionuclide that binds to sulfhydryl groups, using one or more pendant sulfhydryl groups as endogenous ligands and optionally using an exogenous ligand which further stabilizes the bound radiometal ion. More particularly, the invention relates to a method and kit for direct radiolabeling of Fab or Fab' antibody fragments.

The present invention provides certain improvements over the general methods disclosed in Shochat et al., U.S. patent application Ser. No. 07/176,421, filed Apr. 1, 1988, now U.S. Pat. No. 5,061,641.

It is known that certain radiometals display affinities for sulfur ligands, including, e.g., Tc-99m from reduced pertechnetate, Re-186 and Re-188 ions, Cu-67 ions, Hg-197 ions and Bi-212 ions. Some of these radiometals have been bound to proteins, especially antibodies or antibody fragments, using conjugated chelating groups such as diethylenetriaminepentaacetic acid (DTPA) or a variety of sulfur/nitrogen ($S_2N_2$) chelators such as bis-thiosemicarbazones and the like.

Methods have been reported for binding Tc-99m ions directly to antibodies by pre-tinning the protein and then contacting the resultant material with pertechnetate. This procedure often does not work well and some of the radiometal is bound to sites which are comparatively labile in the presence of blood and other bodily fluids or tissues. The mechanism of the pre-tinning process is not well understood and the reasons for production of labile sites of labeling have not been elucidated.

It is also known that proteins containing disulfide bonds can be reduced to produce pendant sulfhydryl groups. If the disulfide bonds link polypeptide chains which are not themselves joined, e.g., antibody light-/heavy chains, reductive cleavage thereof can dissociate the protein into smaller fragments. An example of this is the reductive cleavage of antibody F(ab')$_2$ fragments to form Fab' fragments using disulfide reducing agents such as cysteine, dithiothreitol, mercaptoethanol and the like.

Direct labeling of a protein has the advantage that chelate conjugates are obviated. However, attempts to use such radiolabeled proteins for in vivo applications, e.g., antibody-targeted tumor imaging and therapy, have revealed problems due to loss of the label to other organs which retain it and cause both high background for certain types of imaging and slow clearance of the label from organs such as the liver, spleen and kidneys. The latter problem can in turn cause hepatic and/or renal crisis for the therapy patient due to severe compromise of the affected organ by the high levels of radiation.

It has been discovered that the presence of certain disulfide reducing agents having free -SH groups (e.g. cysteine) can interfere with subsequent labeling, due to binding of the radionuclide cations to the free -SH groups of the reducing agents. In such cases a purification step is required to remove the reducing agent before the product is labeled.

A need exists for a direct method for radiolabeling a monovalent antibody fragment that produces a good yield of a stable radiolabeled product which retains the label in the presence of blood and other body fluids and tissues, and which does not require a purification step to remove a disulfide reducing agent.

OBJECTS OF THE INVENTION

Accordingly, one object of the present invention is to provide a method for direct radiolabeling of a monovalent antibody fragment with a radiometal which does not require removal of excess disulfide reducing agent after bond cleavage.

Another object of the present invention is to provide a method for direct radiolabeling of a monovalent antibody fragment with a radiometal which does not require conjugation to the fragment of a chelator for ions of the radionuclide.

Still another object of the invention is to provide a method of further stabilizing sulfhydryl-bound radiometal ions on a monovalent antibody fragment.

A further object of the invention is to provide a method for radiolabeling a fragment which produces high yields of labeled product with minimal contamination with by-products.

Yet another object of the invention is to provide a convenient and efficient radiolabeling method and kit for use in introducing a radionuclide into a monovalent antibody fragment.

Upon further study of the specification and appended claims, further objects and advantages of this invention will become apparent to those skilled in the art.

SUMMARY OF THE INVENTION

The foregoing objects are achieved by providing a method for producing a radionuclide-labeled monovalent antibody fragment which comprises the steps of cleaving a divalent antibody fragment using sulfite or meta-bisulfite to produce a monovalent antibody fragment having a free sulfhydryl group, and contacting the monovalent antibody fragment with a cation of a metallic radionuclide which binds to sulfhydryl groups, without removing excess sulfite or meta-bisulfite. In a preferred embodiment, the monovalent antibody fragment is a Fab or Fab' fragment.

The method of the invention is advantageously applied to label monovalent antibody fragments with radionuclides such as Tc-99m in a procedure which is simple and practical for the nuclear medicine physician.

The invention also provides kits for effecting the labeling process of the invention.

DETAILED DESCRIPTION

The present inventors have found that a monovalent antibody fragment having free pendant sulfhydryl groups can selectively bind radiometal ions to the sulfhydryl groups that are quite stable in blood and other bodily fluids and tissues. Attempts to repeat pretinning procedures of others with F(ab')$_2$ antibody fragments were unsuccessful in achieving Tc-99m labeling. Further investigation revealed that failure to incorporate the Tc-99m label correlated with absence of monovalent fragments containing free sulfhydryl groups in the pre-tinned material. As disclosed in the related application, Ser. No. 07/176,421, now U.S. Pat. No. 5,061,641, reduction of the F(ab')$_2$ fragment with cysteine, followed by separation of the excess reducing agent on a short sizing gel column, and addition of the resultant Fab'-SH fragment to reduced pertechnetate resulted in binding of all of the reduced pertechnetate to the Fab'-SH. However, certain of the reducing agents disclosed therein (e.g. cysteine, dithiothreitol, 2-mercaptoethanol or the like) can interfere with the subsequent binding of the metallic radionuclide to the fragment, due to the presence of -SH groups in these reducing agents. This interference makes separation of excess reducing agent prior to radiolabeling necessary.

It is of particular interest to produce directly labeled monovalent antibody fragments, such as Fab' fragments. The present inventors have discovered that the use of sulfite or meta-bisulfite as the disulfide reducing agent has the heretofore unrecognized advantage of enabling production of monovalent antibody fragments which are directly labeled with sulfhydryl-binding radiometal ions, without the requirement for a separation step. This is due to the fact that sulfite and meta-bisulfite have no pendant -SH groups which could react with the radiometal ions in competition with the protein having free pendant -SH groups.

Antibodies contain one or more disulfide bonds which link the heavy chains, as well as disulfide bonds which join light and heavy chains together. The latter disulfide bonds are normally less accessible to disulfide reducing agents and the bonds linking heavy chains can normally be selectively cleaved. The resultant fragments retain their immunospecificity and ability to bind to antigen. It will be understood that reduction of disulfide bonds linking the heavy chains of an immunoglobulin must be effected with care, since the normally less reactive disulfide bonds linking light and heavy chains will eventually be reduced if reducing conditions are too drastic or the reducing agent is left in contact with the fragments for too long a time.

The term "monovalent antibody fragment" as used herein denotes Fab' and Fab fragments, normally obtained by cleavage of bivalent fragments or intact immunoglobulin. Fab' antibody fragments are normally and conveniently made by reductive cleavage of F(ab')$_2$ fragments, which themselves are normally made by pepsin digestion of intact immunoglobulin. Fab antibody fragments can be made by papain digestion of intact immunoglobulin, under reducing conditions, or by cleavage of F(ab)$_2$ fragments which result from careful papain digestion of whole Ig. Parham et al., J. Immunol. Methods, 53:133-173, 1982, and Boguslawski et al., J. Immunol. Methods, 120:51-56, 1989, show papain digestion of murine monoclonal IgG$_1$ to F(ab)$_2$. Activation of the papain with thiol, followed by removal of the thiol prior to cleavage, permits cleavage of those immunoglobulins having the papain cleavage site below at least one disulfide bond to occur without further cleavage of the bivalent fragment.

A Fab fragment containing at least one free sulfhydryl group will be termed "Fab-SH" herein. A Fab' with at least one free sulfhydryl group will be termed "Fab'-SH".

It will be appreciated, however, that monovalent fragments can also include any fragments retaining the hypervariable, antigen-binding region of an immunoglobulin and having a size similar to or smaller than a Fab' fragment. This will include genetically engineered and/or recombinant proteins, whether single-chain or multiple-chain, which incorporate an antigen binding site and otherwise function in vivo as targeting vehicles in substantially the same way as natural monovalent immunoglobulin fragments.

It will also be understood that the monovalent antibody fragments to be radiolabeled can be fragments which bind to antigens which include but are not limited to antigens produced by or associated with tumors, infectious lesions, microorganisms, parasites, myocardial infarctions, atherosclerotic plaque, or normal organs or tissues.

It will also be understood that use of the labeling method and kit of the invention is not limited to the preferred monovalent antibody fragments. Rather, the inventive method and kit may be used to bind radiometals to any protein, such as albumin, enzymes, hormones, immune modulators and the like, which contain disulfide groups, normally linked through a cystine residue. These proteins can be treated with the presently recited sulfite or meta-bisulfite reducing agents to generate sulfhydryl groups. This may result in fragmentation of the protein if the disulfide bond links polypeptide chains which are not continuous, or it may merely result in chain separation, possibly involving a change in conformation of the protein if the disulfide bond joins remote segments of a single polypeptide chain. Sulfhydryl groups can be introduced into a polypeptide chain by conventional methods, e.g., use of Traut's Reagent, i.e., iminothiolane, using conventional conditions, e.g., those disclosed in Blattler et al., Biochem., 24:1517-1524, 1985.

The present method is particularly well suited to radiolabeling Fab-SH or Fab'-SH fragments, since they can be generated by reductive cleavage of divalent F(ab)$_2$ or F(ab')$_2$ fragments with the presently claimed sulfite or meta-bisulfite reducing agents. Sulfite cleavage of disulfide bonds yields an S-sulfonate group and a free sulfhydryl group. Sulfitolysis of F(ab')$_2$ generates Fab' molecules containing free sulfhydryl groups which can be subsequently labeled with a cation of a metallic radionuclide which binds to sulfhydryl groups. Likewise, sulfitolysis of F(ab)$_2$ generates Fab fragments having free sulfhydryl groups available for radionuclide labeling. Use of reducing agents such as stannous ion to convert certain radiometal ions, e.g., pertechnetate and perrhenate, to lower oxidation state cations, can convert the S-sulfonate to sulfhydryl.

Reduction is preferably effected at pH 5.0–9.0, preferably 5.0–7.0, e.g., in citrate, acetate or phosphate buffer, and advantageously under an inert gas atmosphere (e.g. nitrogen or argon). Reduction is faster at higher pH, but reoxidation is also faster, and the optimal pH will be one where reduction is reasonably rapid, but reoxidation is negligible. Conditions must be adjusted to maximize cleavage of inter-heavy chain disulfide bonds while minimizing cleavage of disulfide bonds between heavy and light chains. That is, the ratio of disulfide reducing agent to protein is a function of interchain disulfide bond stabilities and must be optimized for each individual case. Cleavage of F(ab')$_2$ or F(ab)$_2$ antibody fragments to Fab' or Fab, respectively, is advantageously effected with about 5–50 mM sodium sulfite or sodium meta-bisulfite, preferably 30–45 mM, and a protein concentration of between about 2 and 10 mg/ml, preferably about 5 mg/ml, in about 30–90 minutes at either room temperature or 37° C.

The Fab-SH or Fab'-SH fragments can be generated in situ and the resultant solution combined with a solution of the radiometal ions to be used for labeling. Alternatively, the Fab-SH or Fab'-SH can be kept at low temperature, e.g., in the refrigerator, for several days to several weeks, preferably at a pH of 3.5–5.5, more preferably at pH 4.5–5.0, advantageously under an inert gas atmosphere, e.g., nitrogen or argon.

It is convenient to lyophilize the Fab-SH or Fab'-SH for ease of storage and stabilization. This is advantageously effected at pH of about 5.5, from a solution of a volatile buffer, e.g., ammonium acetate, and preferably also in the presence of a stabilizer to prevent aggregation, e.g., a sugar such as trehalose or sucrose. Such lyophilization conditions are conventional and well known to the ordinary skilled artisan. The solution of antibody fragment also can be frozen and then thawed prior to use, but this carries greater risk of reoxidation and aggregation of the protein.

Radiometals which can be bound to proteins using the present method are those which have a strong affinity for sulfhydryl groups. Generally, these will be metal ions which form relatively insoluble sulfides in the conventional qualitative analysis schemata. These include, but are not limited to, Tc-99m, Re-186, Re-188, Cu-67, Hg-197, Pb-203, Pb/Bi-212 and the like. Radiometals having a gamma emission energy in the range of about 50–500 KeV are useful for scintigraphy. Positron emitters can also be used for imaging applications. Beta and alpha emitters are useful for therapy. Technetium-99m is a preferred radiolabel for scintigraphy because of its ready availability and ease of preparation from commercial pertechnetate generators.

Rhenium is found just below technetium in the periodic table, has the same outer shell electronic configuration, and therefore is expected to have very similar chemical properties, especially the behavior of analogous compounds. In fact, rhenium compounds behave similarly to technetium compounds insofar as reduction and chelation are concerned but their greater susceptibility to oxidation requires greater care in handling.

The radioisotope Re-186 is attractive for both imaging and therapy. It has a half-life of about 3.7 days, a high LET beta emission (1.07 MeV) and a convenient gamma emission energy (0.137 MeV). Like technetium, rhenium is produced from perrhenate, and the reduced rhenium ions can bind non-specifically to protein. Accordingly, a method for Re-186 labeling of proteins, wherein the reduced perrhenate is bound to sulfhydryl groups of a protein molecule such as an antibody, would be advantageous. Re-188 is a generator-produced beta and gamma emitter with a half-life of about 17 hours and could be useful for imaging and therapy.

Copper ions are also complexed by sulfur chelators. Cu-67 is another attractive radionuclide for imaging and therapy. It has a half-life of about 2.6 days, a beta emission (0.570 MeV) and a gamma emission (0.185 MeV), although the beta energy is relatively low. Cu-67 is relatively expensive and not readily available at present, although such conditions can change as demand develops. It has the advantage that it forms tight chelates with thiols, the labeling is simple and rapid, and requires no reducing agent for the radiometal.

Other radionuclides with similar chelation behavior to copper, e.g., mercury and lead, also could be bound to thiol-containing compounds according to the method of the invention. Hg-197 has a half-life of about 1.5 days, and emits gamma radiation in an energy range of 78–268 KeV, and Pb-203 is a strong gamma-emitter at about 275 KeV, with a half-life of about 51 hr, making them suitable for gamma scintigraphy. Bi-212 is an alpha-emitter with a half-life of about 1 hr and an energy of 6.09 MeV, making it of considerable interest for in vivo therapy. It is produced in situ from a Pb-212 precursor with emission of gamma radiation of 239 KeV, with a half-life of about 10.6 hr. Thus, antibody conjugates for Bi-212 therapy will be Pb-212-labeled conjugates, and the short-hand notation lead/bismuth or Pb/Bi is used herein to indicate this. It will be understood that the invention is not limited to the exemplified radiometal ions, but is generally applicable to ions that bind tightly to sulfhydryl groups.

By "reduced pertechnetate" or "reduced perrhenate" is meant the species of technetium or rhenium ion formed by chemical reduction of pertechnetate or perrhenate and chelated by the thiol group(s). It is generally thought that reduced pertechnetate is in the form of Tc(III) and/or Tc(IV) and/or Tc(V) in such chelates, and that reduced perrhenate is in the form of Re(III) and/or Re(IV) and/or Re(V), but higher or lower oxidation states and/or multiple oxidation states cannot be excluded and are within the scope of the invention. Copper will normally be in the form of Cu(II), although Cu(I) and/or Cu(III) are not excluded. Mercury will normally be in the form of Hg(I) and/or Hg(II). Lead/bismuth will normally be in the form of Pb(II) or Pb(IV).

Technetium labeling of the sulfhydryl-containing protein is generally effected by conventional methods. Pertechnetate is obtained from a commercially available generator, most commonly in the form of $NaTcO_4$, normally in saline solution. Other forms of pertechnetate may be used, with appropriate modification of the procedure, as would be suggested by the supplier of a new form of generator or as would be apparent to the ordinary skilled artisan.

Reduction is effected by any of a variety of conventional reducing agents, preferably stannous ion, generally in aqueous solution. Other suitable reducing agents include, e.g., dithionite, borohydride, ferrous ion and the like. It will be appreciated that stannous ion can be generated in situ from tin metal, e.g., foil, granules, powder, turnings and the like, by contact with aqueous acid, e.g., HCl.

Pertechnetate is generally used at an activity of about 5–50 mCi/ml preferably about 20–30 mCi/ml, in saline, e.g., 0.9% ("physiological") saline, buffered at a pH of about 3–7, preferably 3.5–5.5, more preferably about 4.5–5.0. Suitable buffers include, e.g., acetate, tartrate, citrate, phosphate and the like.

When stannous ion is used, it is normally added in excess, to assure complete reduction and utilization of the pertechnetate and to reduce $SSO_3H$ to sulfhydryl. The stannous ion concentration is generally in the range of $10^{-4}$–$10^{-3}$N, and it is usually added in the form of an aqueous mineral acid solution, e.g., $SnCl_2$/0.1N HCl.

The reduction is normally effected under an inert gas atmosphere, e.g., nitrogen, argon or the like. The reaction temperature is generally maintained at about room temperature, e.g., 18°–25° C., and the reaction usually requires about 0.5–3 hrs for substantial completion.

It is often advantageous to add a transchelating agent and/or a stabilizing agent for the stannous ion. It is known that ascorbate can improve specific loading of a chelator with reduced pertechnetate and minimize formation of $TcO_2$, when the reducing agent is stannous ion, although the combination of ascorbate with certain sulfhydryl-containing proteins has been known to have deleterious effects on the protein. Other polycarboxylic acids, e.g., tartrate, citrate, phthalate, iminodiacetate, ethylenediaminetetraacetic acid (EDTA), diethylenetriaminepentaacetic acid (DTPA) and the like, can also be used.

Such agents can play one or more roles in the labeling process. On the one hand, they chelate stannous ion and may prevent adventitious reactions and/or promote reduction by stabilization of stannic ions, and they may also chelate—and thereby stabilize—certain oxidation states of reduced pertechnetate and perrhenate, thereby serving as transchelating agents for the transfer of these technetium and rhenium ions to the presumably more stable chelation with one or more thiol groups and other nearby ligands on the protein. Such agents will be referred to as "transchelators" herein.

The transchelator forms a chelate with the technetium or rhenium ion that readily and rapidly loses the ion to the sulfur atom(s) of the sulfhydryl group(s) and possibly nearby amine and/or carboxyl groups from lysine or aspartate/glutamate residues. Although polycarboxylic acids are mentioned, by way of illustration, any of a variety of anionic and/or hydroxylic oxygen-containing species could serve this function, e.g., salicylates, acetylacetonates, hydroxyacids, catechols, glycols and other polyols, e.g., glucoheptonate, and the like. The molar ratio of transchelator to sulfhydryl-containing protein should be about 100:1–1:1, preferably 50:1–20:1, more preferably about 10:1.

The transchelator can be immobilized on a solid support and used to separate reduced pertechnetate or perrhenate from the remaining components of the reducing system used for their generation, or it can be used to retain a radiometal in a form which will permit rapid transfer to sulfhydryl groups of a protein. The advantage of such an expedient is that substantially only the radiometal ion is transferred to the protein when a solution thereof is contacted with the solid phase bearing the chelated radiometal ions. Physical separation of the solid phase will then leave labeled protein, uncontaminated by other ions or components of the labeling reagent system. Ideally, the resultant labeled protein could be used directly as an injectable.

It may be desirable to remove unreacted radiometal and/or reducing agent from the labeled protein. This can be accomplished by adding scavengers for the ions, e.g., chelators which can be similar to the transchelators. An alternative to adding such scavengers is passage of the reduction mixture through a column containing derivatized adsorbants capable of trapping pertechnetate, e.g., gel columns with bound chelators for reduced pertechnetate and/or stannous/stannic ions. For example, a polymer column packing with bound iminodiacetic acid, called "Chelex", is available from BioRad. Other such suitable column packings include polymers or gels modified to contain DTPA, EDTA and the like, a number of which are commercially available. The same solid phase bound ligand can be used for transchelation and scavenging, in appropriate cases.

A scavenger for free sulfhydryl groups can be added to the reaction mixture after binding to the radiometal is substantially complete. Suitable such scavengers include, e.g., maleimide, iodoacetamide, iodoacetic acid and the like. After initial determination of the extent of uptake of radiometal by the thiol-containing compound, an amount of scavenger capable of reacting with substantially all of the remaining sulfhydryl groups is used. The excess of such sulfhydryl group scavengers can be further scavenged, if desired, by e.g., cysteine or similar such thiol compound, to render them more soluble and thus more readily excretable, so that the conjugation reaction mixture can be used directly as an injectable preparation. Alternatively, a further separation of low molecular weight materials can be effected prior to injection of the labeled protein.

Rhenium labeling will be effected in substantially the same manner as technetium labeling, with special care being taken to insure the absence of air or oxygen in the system. Re-188 is produced in the form of sodium perrhenate by use of a generator analogous to currently available technetium generators.

Copper labeling will be effected by reaction of a thiol-containing protein with a solution of copper ions, normally Cu(II) ions, in the form of a convenient salt, e.g., chloride, citrate, tartrate or the like, either as available or by mixing of, e.g., the chloride with, e.g., sodium, potassium or ammonium citrate, tartrate or the like. Cu-67 is currently available as $CuCl_2$ from Oak Ridge National Laboratories, Tennessee, or from Los Alamos National Laboratories, New Mexico.

Other metallic alpha-, beta-, gamma- and/or positron-emitting radionuclides which bind preferentially to sulfhydryl groups, e.g., Hg-197, Pb-203, Pb-212, and which are available as salts, or in forms which can be readily converted to salts, can also be chelated using the chelators of the present invention. They can be used advantageously, as radiolabels for imaging or as radiotherapeutic agents, in the form of antibody/fragment conjugates prepared according to the method of the invention. Chelation to the antibody protein is effected analogously to Cu-67 labeling.

Mercury radioisotopes are normally available as $HgCl_2$ or as $Hg(NO_3)_2$, e.g., from Oak Ridge National Laboratories.

Lead/bismuth radioisotopes are normally available from Argonne National Laboratories in the form of a supported radon generator.

An important embodiment of the present invention involves the further stabilization or "capping" of a thiol-bound radiometal ion with one or more exogenous ligands. These will generally be designed to complete the coordination sphere of the ion and to complement the sulfhydryl group(s) already provided by the protein. A balance must be struck between ligands that bind the ion so tightly that they weaken the sulfur-metal bond(s) to the protein thiol group(s) and reduce the stability of the radiometal label in serum, and those that provide insufficient chelating power so that the ion is easily extracted from the protein by other exogenous ligands in serum or bone marrow, or in organs such as the liver, spleen or kidneys where clearance occurs.

It must be recognized that the present approach is quite different from prior art approaches, where a multidentate ligand is first conjugated to a protein and then must be loaded with a radiometal ion to form the chelate conjugate, or where a multidentate ligand is first loaded with a radiometal ion and then conjugated to a protein. The present invention contemplates chelation of the radiometal ion with one or more thiol groups on the protein, with at least one coordination site of the ion available for binding to an exogenous ligand having superior coordinating ability to water and amine/carboxyl ligands on the protein or a transchelator added to the initial labeling solution. Only after the ion binds to one or two sulfhydryl groups is the exogenous ligand added, to fill remaining coordination sites and cap the ion.

The exogenous ligand can be monodentate or multidentate, and preferably contains at least one sulfur atom or other soft base electron pair donor group, so that it can displace weaker donor ligands in the radiometal ion coordination sphere and bind to the ion more tightly than the ligands it displaces. The function of the exogenous ligand is, in the first instance, to cap the ion and make the resultant chelate stable to further incursions which would strip the label from the protein, by enveloping the metal ion and shielding it from contact with extraneous ligands from, e.g., serum components.

Examples of such exogenous capping ligands include, e.g., monodentate sulfur/phosphorus compounds, such as simple thiols, e.g., $C_{1-30}$ mercaptoalkanes, thioesters, thioamides, thioureas, phosphines, phosphonates and the like. Bidentate ligands of the S/S, S/N, P/N and like varieties are also suitable, especially S/N ligands, e.g., mercaptopurine, 2-aminoethylamine and the like. Tridentate S/S/N, S/N/N, and analogous phosphorus ligands, especially S/N/N ligands, can also be used. The foregoing are merely representative of the myriad types and varieties of such capping ligands that can be used to stabilize the radiometal bound to the sulfhydryl group on the protein.

Further functions can, however, be envisioned for this ligand. For example, the exogenous ligand could bear carbohydrate polymer or polyol groups to make the resultant radiometal chelate less immunogenic and to further protect it against loss of the label. Examples include any of the foregoing ligands which are linked to, e.g., dextran, polysaccharides, polyethylene glycol (PEG), and the like.

Alternatively, the exogenous ligand could bear solubilizing groups that would aid in the clearance and excretion of small metabolites of the fragment, along with the radiometal. Examples include any of the foregoing ligands which also bears additional carboxyl, hydroxyl, sulfonate or like groups. Metabolism of the fragment would produce short oligopeptides bearing the solubilizing groups and the latter metabolites would be more readily excreted in the urine rather than retained by the kidneys, resulting in damage to that vital organ.

A rather different function for the exogenous ligand could be to serve as a cytotoxic agent to complement and/or potentiate the radioisotope or to serve as a therapeutic agent or carrier for a therapeutic agent. One embodiment is to join a radiosensitizer to an exogenous capping ligand for use to potentiate the cytotoxic effects of a radiotherapeutic metal isotope.

Certain cytotoxic drugs are themselves candidates for use as capping ligands, e.g., 6-mercaptopurine.

The foregoing list is by no means exhaustive, and other functions, such as to enhance targeting, reduce the rate of clearance of circulating or targeted radiolabeled fragments, change the biodistribution of the labeled fragments or the like, can be envisioned and fall within the broad scope of the present invention.

A kit for use in radiolabeling a monovalent antibody fragment, such as a Fab'-SH fragment, with a metallic radionuclide such as Tc-99m (illustrative of the general method, with variations that would be apparent to the ordinary skilled artisan), would include, in its simplest form, the following reagents, in suitable containers, preferably sterile and under an inert gas atmosphere:
1. lyophilized, preferably stabilized, monovalent antibody fragment, e.g., Fab'-SH, prepared from sulfite or metabisulfite reduction of the corresponding divalent antibody fragment without removal of the sulfite or meta-bisulfite; and
2. radionuclide ions or reagents for their generation. Normally, the kit is used and/or provided in combination with one or more auxiliary reagents, buffers, filters, vials, columns and the like for effecting the radiolabeling steps.

One example of such a kit would include:
1. lyophilized Fab'-SH, stabilized with sucrose;
2. lyophilized $SnCl_2$;
3. phosphate-buffered saline (PBS), preferably containing a transchelator such as tartrate, citrate, EDTA, glucoheptonate or the like;
4. metal-free 10N HCl to dissolve the $SnCl_2$; and
5. PBS or buffer 3 to dilute the $SnCl_2$, together with sterile, argon-purged vials and syringes for effecting transfers and sterile filters for removing contaminants.

An alternative kit could contain a single vial having therein lyophilized, buffered Fab'-SH and a stannous salt, e.g., stannous tartrate, stabilized with sucrose; together with a sterile, argon-purged vials and syringes for collecting and transferring pertechnetate or perrhenate from a generator, and a sterile syringe and filter cartridge for removing labeled antibody fragment for administration to the patient.

Stannous glucoheptonate is commercially available for reduction of pertechnetate and can be used in place of stannous chloride or tartrate. Additionally, a kit containing $F(ab')_2$ or $F(ab)_2$ together with reducing reagents, e.g., sodium sulfite or sodium meta-bisulfite, can be supplied for in situ Fab'-SH or Fab-SH generation.

The foregoing are merely illustrative and many variants can be envisioned for use with the variations in the process of the invention described hereinabove.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLES

Example 1. Preparation of Tc-99m-anti-CEA-Fab' a) Preparation of Fab'-SH

Monoclonal anti-CEA-$F(ab')_2$ at 5 mg/ml in 0.04M phosphate buffered saline (PBS), pH 7.2, is treated with 30 mM sodium metabisulfite or 45 mM sodium sulfite prepared in 0.04M PBS, pH 7.2. The reaction mixture is flushed with argon for 2 minutes. The cleavage proceeds quantitatively to Fab' in 60 minutes at room temperature.

b) Preparation of Fab'-SH in Labeling Buffer

A stock solution of $SnCl_2$ containing 3350 mg $SnCl_2 \cdot 2 H_2O$ in 1 ml concentrated HCl is prepared. The solution is diluted to 0.075M $SnCl_2$ with dd$H_2O$ that has been purged with argon. An 0.1M sodium potassium tartrate (NKT) solution in 0.05M NaAc, pH 5.5, is prepared and purged with argon. One volume of 0.075M $SnCl_2$ is mixed with 26 volumes of the 0.1M NKT solution, filtered and purged with argon to produce the labeling buffer. The labeling buffer is added to anti-CEA-Fab'-SH to yield 123 μg Sn/mg anti-CEA-Fab'-SH.

c) Tc-99m Labeling

99m-TcO$_4$ is then added (about 20 mCi/mg in saline), at room temperature, and incubated about 5 to 30 min. The resultant labeled antibody solution contains nearly 100% of the label bound to Fab', and can be used after sterile filtration through a syringe needle equipped with a sterile filter, directly for patient injection.

d) Lyophilization and Labeling

To the anti-CEA-Fab'-SH in labeling buffer prepared according to 1(b), above, 1M sucrose is added to yield 0.09M sucrose. The anti-CEA-Fab'-SH mixture is filled into sterile vials (1.25 mg anti-CEA-Fab'-SH/vial) and lyophilized. The vacuum is broken with an inert gas and the vials are removed, stoppered and crimp sealed.

In use, the vial contents are reconstituted with 20 mCi 99m-TcO$_4$. Labeling proceeds for about 5 minutes. If the Tc-99m incorporation is less than about 95%, the radiolabeled sample can be purified by a desalting cartridge prior to injection.

Example 2. Radioimmunodetection of animal tumors with Tc-99m-anti-CEA-Fab'

Biodistribution studies in nude mice bearing LS174T tumors indicate that Tc-99m-anti-CEA-Fab', produced from sulfitolysis of F(ab')$_2$ as in Example 1, is comparable to the control, which is Tc-99m-anti-CEA-Fab' created by cysteine reduction. Positive tumor to non-tumor ratios are seen in all organs at 24 hours, except for the kidney.

Example 4. Radioimmunodetection of lung tumor with Tc-99m-anti-CEA-Fab'

A sterile solution of Tc-99m-anti-CEA-Fab', prepared as in Example 1, is infused intravenously into a female patient having metastatic lung cancer with involvement in both right and left lobes. As early as 1.75 hr after injection of the radiolabeled fragment, the tumors in both lungs can be detected, with improved imaging after 2-5 hr. The same patient is imaged with I-123-anti-CEA-Fab' and similar results are obtained. Negligible liver uptake of the label is seen after 2 hr and the lung involvement is readily detected, despite some blood pool activity nearby. A lesion about 1.2×2 cm in size is detectable.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method for producing a radionuclide-labeled monovalent antibody fragment which comprises the steps of:
    (a) cleaving a divalent F(ab)$_2$ or F(ab')$_2$ antibody fragment using sulfite or meta-bisulfite ions to produce monovalent Fab or Fab' antibody fragments having free sulfhydryl and S-sulfonate groups;
    (b) contacting said monovalent Fab or Fab' antibody fragments with a sufficient amount of stannous ions to reduce said S-sulfonate groups to free sulfhydryl groups and to reduce radiopertechnetate or radioperrhenate ions added subsequently; and
    (c) contacting said monovalent Fab or Fab' antibody fragments having free sulfhydryl groups with radiopertechnetate or radioperrhenate ions, without removing excess sulfite or meta-bisulfite ions, to produce radionuclide-labeled monovalent Fab or Fab' antibody fragments having reduced radiopertechnetate or radioperrhenate ions bound to said sulfhydryl groups.

2. A method as claimed in claim 1, wherein in step (c), 99m-pertechnetate is used.

3. A method as claimed in claim 2, wherein in step (c), said contacting is effected in the presence of a transchelator for reduced pertechnetate ions.

4. A method as claimed in claim 1, wherein in step (c), 186- or 188-perrhenate is used.

5. A method as claimed in claim 4, wherein in step (c), said contacting is effected in the presence of a transchelator for reduced perrhenate ions.

6. A method as claimed in claim 1, wherein said cleaving step is carried out using about 5-50 mM sulfite or metabisulfite ions.

7. A method as claimed in claim 6, wherein said cleaving step is carried out using 30-45 mM sulfite or meta-bisulfite ions.

8. A method as claimed in claim 1, wherein said cleaving step is carried out at a protein concentration of about 2-10 mg/ml.

9. A method as claimed in claim 8, wherein said protein concentration is about 5 mg/ml.

10. A method as claimed in claim 1, which is carried out at a pH of about 5.0-9.0.

11. A method as claimed in claim 10, which is carried out in an acetate, phosphate or borate buffer containing about 0.15M NaCl.

12. A method as claimed in claim 1, which is carried out in an inert gas atmosphere.

13. A method as claimed in claim 1, wherein said radionuclide-labeled monovalent Fab or Fab' antibody fragments produced in step (c) are contacted with an exogenous ligand which binds to the sulfhydryl-bound reduced radiopertechnetate or radioperrhenate ions, and the resultant stabilized, radionuclide-labeled Fab or Fab' fragments are recovered.

14. A method as claimed in claim 13, wherein said exogenous ligand has a sugar, dextran or polyol moiety joined thereto to render it hypoimmunogenic.

15. A method as claimed in claim 13, wherein said exogenous ligand includes a radiosensitizer.

16. A method for producing a radionuclide-labeled protein which comprises the steps of:
    (a) cleaving disulfide bonds in a protein containing disulfide bonds using sulfite or meta-bisulfite ions to produce an intermediate protein having free sulfhydryl and S-sulfonate groups;
    (b) contacting said intermediate protein with an amount of stannous ions sufficient to reduce said S-sulfonate groups to free sulfhydryl groups and to reduce radiopertechnetate or radioperrhenate ions added subsequently; and
    (c) contacting said intermediate protein having free sulfhydryl groups with radiopertechnetate or radioperrhenate ions, without removing excess sulfite or meta-bisulfite ions, to produce a radionuclide-labeled protein having reduced radiopertechnetate or radioperrhenate ions bound to said sulfhydryl groups.

17. A method as claimed in claim 16, wherein in step (c), 99m-pertechnetate is used.

18. A method as claimed in claim 17, wherein in step (c), said contacting is effected in the presence of a transchelator for reduced pertechnetate ions.

19. A method as claimed in claim 16, wherein in step (c), 186- or 188-perrhenate is used.

20. A method as claimed in claim 19, wherein in step (c), said contacting is effected in the presence of a transchelator for reduced perrhenate ions.

21. A method as claimed in claim 16, wherein the radionuclide-labeled protein produced in step (c) is contacted with an exogenous ligand which binds to the sulfhydryl-bound reduced radiopertechnetate or radioperrhenate ions, and the resultant stabilized, radionuclide-labeled protein is recovered.

22. A method as claimed in claim 16, wherein said protein containing disulfide bonds is selected from the group consisting of albumin, an enzyme, a hormone and an immune modulator.

* * * * *